United States Patent [19]

Clark et al.

[11] Patent Number: 4,868,119

[45] Date of Patent: Sep. 19, 1989

[54] HEMATOPOIETIC GROWTH FACTORS

[75] Inventors: Steven C. Clark, Winchester; Gordon G. Wong, Cambridge, both of Mass.

[73] Assignee: Genetics Institute, Inc., Cambridge, Mass.

[21] Appl. No.: 940,362

[22] Filed: Dec. 11, 1986

[63] Continuation-in-part of Ser. No. 860,377, May 6, 1986.

[51] Int. Cl.[4] .................... C12N 1/20; C12N 15/00; C12N 1/00

[52] U.S. Cl. ............................ 435/240.2; 435/172.3; 435/320; 435/252.31; 435/252.33; 536/27; 935/9; 935/11; 935/13

[58] Field of Search .................. 435/70, 172.3, 320, 435/253; 935/9, 11, 13; 536/27

[56] References Cited

U.S. PATENT DOCUMENTS

4,438,032  3/1984  Golde et al. .................... 435/172.3

FOREIGN PATENT DOCUMENTS

0261592  3/1988  European Pat. Off.
0276551  8/1988  European Pat. Off.

OTHER PUBLICATIONS

Gough et al, Haematology and Blood Transfusion, vol. 29, pp. 380–384 (1985).
Wong et al, Science, vol. 228, pp. 810–815 May 17, 1985.
Wong et al., Cancer Cells 3, Growth Factors and Transformation, Cold Spring Harb. Lab. pp. 235–242 (1985).
Ralph, Leukocytes and Host Defense, 17th International Leucocyte Culture Conf. pp. 235–242, 1986.
Dunn et al, Cancer Cells 3, Growth Factors and Transformation, Cold Spring Harb. Lab. pp. 227–234 (1985).
Kawasaki et al, Science, vol. 230, pp. 291–296, Oct. 18, 1985.
Lusis et al, Nature, vol. 298, pp. 75–77, Jul. 1, 1982.
Gough et al, Nature, vol. 309, pp. 763–767, Jun. 28, 1984.
Gough et al, The EMBO J., vol. 4, pp. 645–653, Mar. 1985.
Hitzeman et al., Science, vol. 219, pp. 620–625, Feb. 11, 1983.
Kaufman et al, Mol. and Cell. Biol. vol. 2, pp. 1304–1319, Nov. 1982.
Miyatake et al, The EMBO J. vol. 4, pp. 2561–2568.
Chen, et al., "Granulocyte/Macrophage Colony–Stimulating Factor Stimulates Monocyte and Tissue Macrophage Proliferation and Enhances Their Responsiveness to Macrophage Colony–Stimulating Factor," *Blood* 71(4):997–1002 (Apr. 1988).
Walker, et al., "Hierarchical Down–Modulation of Hemopoietic Growth Factor Receptors," *Cell* 43:269–276, (Nov. 1985).
Ladner, et al., "Human CSF–1: gene structure and alternative splicing of mRNA precursors," *The EMBO Journal* 6(9):2693–2698 (1987).
Wong et al., "Human CSF–1: Molecular Cloning and Expression of 4–kb cDNA Encoding the Human Urinary Protein," *Science* 235 (4795): 1504–1508 (Mar. 20, 1987).
Manos, "Expression and Processing of a Recombinant Human Macrophage Colony–Stimulating Factor in Mouse Cells," *Molecular and Cellular Biology* 8(11): 5035–5039 (Nov. 1988).
Rettenmier, et al., "Differential Processing of Colony–Stimulating Factor 1 Precursors Encoded by Two Human cDNAs", *Molecular and Cellular Biology* 8(11):5026–5034 (Nov. 1988).

*Primary Examiner*—Alvin E. Tanenholtz
*Attorney, Agent, or Firm*—David L. Berstein; Bruce M. Eisen

[57] ABSTRACT

A novel family of primate CSF-1-like polypeptides is provided via recombinant techniques.

4 Claims, 5 Drawing Sheets

Figure 1

```
          10         20         30         40         50         60         70
CCTGGGTCCT CTCGGCGCCA GAGCCGCTCT CCGCATCCCA GGACAGCGGT GCGGCCCTCG GCCGGGCGC 80         90        100        110        120        130        140
CCACTCCGCA GCAGCCAGCG AGCGAGCGAG CGAGCGAGGG CGGCCGACGC GCCCGGCCGG GACCCAGCTG (-32)              160                  175              190
CCCGT ATG ACC GCG CCG GGC GCC GCC GGG CGC TGC CCT CCC ACG ACA TGG CTG
      MET Thr Ala Pro Gly Ala Ala Gly Arg Cys Pro Pro Thr Thr Trp Leu 205              220              235           (1)
GGC TCC CTG CTG TTG TTG GTC TGT CTC CTG GCG AGC AGG AGT ATC ACC GAG GAG
Gly Ser Leu Leu Leu Leu Val Cys Leu Leu Ala Ser Arg Ser Ile Thr Glu Glu 250              265              280              295
GTG TCG GAG TAC TGT AGC CAC ATG ATT GGG AGT GGA CAC CTG CAG TCT CTG CAG
Val Ser Glu Tyr Cys Ser His MET Ile Gly Ser Gly His Leu Gln Ser Leu Gln 310              325              340              355
CGG CTG ATT GAC AGT CAG ATG GAG ACC TCG TGC CAA ATT ACA TTT GAG TTT GTA
Arg Leu Ile Asp Ser Gln MET Glu Thr Ser Cys Gln Ile Thr Phe Glu Phe Val 370              385              400
GAC CAG GAA CAG TTG AAA GAT CCA GTG TGC TAC CTT AAG AAG GCA TTT CTC CTG
Asp Gln Glu Gln Leu Lys Asp Pro Val Cys Tyr Leu Lys Lys Ala Phe Leu Leu 415              430              445              460
GTA CAA GAC ATA ATG GAG GAC ACC ATG CGC TTC AGA GAT AAC ACC CCC AAT GCC
Val Gln Asp Ile MET Glu Asp Thr MET Arg Phe Arg Asp Asn Thr Pro Asn Ala 475              490              505
ATC GCC ATT GTG CAG CTG CAG GAA CTC TCT TTG AGG CTG AAG AGC TGC TTC ACC
Ile Ala Ile Val Gln Leu Gln Glu Leu Ser Leu Arg Leu Lys Ser Cys Phe Thr 520              535              550              565
AAG GAT TAT GAA GAG CAT GAC AAG GCC TGC GTC CGA ACT TTC TAT GAG ACA CCT
Lys Asp Tyr Glu Glu His Asp Lys Ala Cys Val Arg Thr Phe Tyr Glu Thr Pro 580              595          (122)610              625
CTC CAG TTG CTG GAG AAG GTC AAG AAT GTC TTT AAT GAA ACA AAG AAT CTC CTT
Leu Gln Leu Leu Glu Lys Val Lys Asn Val Phe Asn Glu Thr Lys Asn Leu Leu 640              655              670
GAC AAG GAC TGG AAT ATT TTC AGC AAG AAC TGC AAC AAC AGC TTT GCT GAA TGC
Asp Lys Asp Trp Asn Ile Phe Ser Lys Asn Cys Asn Asn Ser Phe Ala Glu Cys 685              700              715              730
TCC AGC CAA GAT GTG GTG ACC AAG CCT GAT TGC AAC TGC CTG TAC CCC AAA GCC
Ser Ser Gln Asp Val Val Thr Lys Pro Asp Cys Asn Cys Leu Tyr Pro Lys Ala
```

Figure 1 (Con't)

```
       745                    760                   775
ATC CCT AGC AGT GAC CCG GCC TCT GTC TCC CCT CAT CAG CCC CTC GCC CCC TCC
Ile Pro Ser Ser Asp Pro Ala Ser Val Ser Pro His Gln Pro Leu Ala Pro Ser 790              805(189)                820                    835
ATG GCC CCT GTG GCT GGC TTG ACC TGG GAG GAC TCT GAG GGA ACT GAG GGC AGC
MET Ala Pro Val Ala Gly Leu Thr Trp Glu Asp Ser Glu Gly Thr Glu Gly Ser 850                    865                   880                895
TCC CTC TTG CCT GGT GAG CAG CCC CTG CAC ACA GTG GAT CCA GGC AGT GCC AAG
Ser Leu Leu Pro Gly Glu Gln Pro Leu His Thr Val Asp Pro Gly Ser Ala Lys 910                   925                  940
CAG CGG CCA CCC AGG AGC ACC TGC CAG AGC TTT GAG CCG CCA GAG ACC CCA GTT
Gln Arg Pro Pro Arg Ser Thr Cys Gln Ser Phe Glu Pro Pro Glu Thr Pro Val 955                   970                  985                 1000
GTC AAG GAC AGC ACC ATC GGT GGC TCA CCA CAG CCT CGC CCC TCT GTC GGG GCC
Val Lys Asp Ser Thr Ile Gly Gly Ser Pro Gln Pro Arg Pro Ser Val Gly Ala 1015                  1030                 1045
TTC AAC CCC GGG ATG GAG GAT ATT CTT GAC TCT GCA ATG GGC ACT AAT TGG GTC
Phe Asn Pro Gly MET Glu Asp Ile Leu Asp Ser Ala MET Gly Thr Asn Trp Val 1060              1075                  1090                 1105
CCA GAA GAA GCC TCT GGA GAG GCC AGT GAG ATT CCC GTA CCC CAA GGG ACA GAG
Pro Glu Glu Ala Ser Gly Glu Ala Ser Glu Ile Pro Val Pro Gln Gly Thr Glu 1120                  1135                 1150                1165
CTT TCC CCC TCC AGG CCA GGA GGG GGC AGC ATG CAG ACA GAG CCC GCC AGA CCC
Leu Ser Pro Ser Arg Pro Gly Gly Gly Ser MET Gln Thr Glu Pro Ala Arg Pro 1180                  1195                 1210
AGC AAC TTC CTC TCA GCA TCT TCT CCA CTC CCT GCA TCA GCA AAG GGC CAA CAG
Ser Asn Phe Leu Ser Ala Ser Ser Pro Leu Pro Ala Ser Ala Lys Gly Gln Gln 1225                  1240                 1255                 1270
CCG GCA GAT GTA ACT GGT ACA GCC TTG CCC AGG GTG GGC CCC GTG AGG CCC ACT
Pro Ala Asp Val Thr Gly Thr Ala Leu Pro Arg Val Gly Pro Val Arg Pro Thr 1285                  1300                 1315
GGC CAG GAC TGG AAT CAC ACC CCC CAG AAG ACA GAC CAT CCA TCT GCC CTG CTC
Gly Gln Asp Trp Asn His Thr Pro Gln Lys Thr Asp His Pro Ser Ala Leu Leu 1330                  1345                 1360                 1375
AGA GAC CCC CCG GAG CCA GGC TCT CCC AGG ATC TCA TCA CTG CGC CCC CAG GGC
Arg Asp Pro Pro Glu Pro Gly Ser Pro Arg Ile Ser Ser Leu Arg Pro Gln Gly 1390                  1405                 1420                1435
CTC AGC AAC CCC TCC ACC CTC TCT GCT CAG CCA CAG CTT TCC AGA AGC CAC TCC
Leu Ser Asn Pro Ser Thr Leu Ser Ala Gln Pro Gln Leu Ser Arg Ser His Ser
```

Figure 1 (Con't)

```
          1450                1465                1480
TCG GGC AGC GTG CTG CCC CTT GGG GAG CTG GAG GGC AGG AGG AGC ACC AGG GAT
Ser Gly Ser Val Leu Pro Leu Gly Glu Leu Glu Gly Arg Arg Ser Thr Arg Asp 1495                1510                1525                1540
CGG AGG AGC CCC GCA GAG CCA GAA GGA GGA CCA GCA AGT GAA GGG GCA GCC AGG
Arg Arg Ser Pro Ala Glu Pro Glu Gly Gly Pro Ala Ser Glu Gly Ala Ala Arg 1555                1570                1585
CCC CTG CCC CGT TTT AAC TCC GTT CCT TTG ACT GAC ACA GGC CAT GAG AGG CAG
Pro Leu Pro Arg Phe Asn Ser Val Pro Leu Thr Asp Thr Gly His Glu Arg Gln 1600                1615                1630                1645
TCC GAG GGA TCC TCC AGC CCG CAG CTC CAG GAG TCT GTC TTC CAC CTG CTG GTG
Ser Glu Gly Ser Ser Ser Pro Gln Leu Gln Glu Ser Val Phe His Leu Leu Val 1660                1675                1690                1705
CCC AGT GTC ATC CTG GTC TTG CTG GCT GTC GGA GGC CTC TTG TTC TAC AGG TGG
Pro Ser Val Ile Leu Val Leu Leu Ala Val Gly Gly Leu Leu Phe Tyr Arg Trp 1720                1735                1750
AGG CGG CGG AGC CAT CAA GAG CCT CAG AGA GCG GAT TCT CCC TTG GAG CAA CCA
Arg Arg Arg Ser His Gln Glu Pro Gln Arg Ala Asp Ser Pro Leu Glu Gln Pro 1765           1780           1795                          1817
GAG GGC AGC CCC CTG ACT CAG GAT GAC AGA CAG GTG GAA CTG CCA GTG TAGAGGGAAT
Glu Gly Ser Pro Leu Thr Gln Asp Asp Arg Gln Val Glu Leu Pro Val 1827       1837       1847       1857       1867       1877       1887
TCTAAGCTGG ACGCACAGAA CAGTCTCTCC GTGGAGGAG ACATTATGGG GGGTCCACCA CCACCCCTCC 1897       1907       1917       1927       1937       1947       1957
CTGGCCATCC TCCTGGAATG TGGTCTGCCC TCCACCAGAG CTCCTGCCTG CCAGGACTGG ACCAGAGCAG 1967       1977       1987       1997       2007       2017       2027
CCAGGCTGGG GCCCCTCTGT CTCAACCCGC AGACCCTTGA CTGAATGAGA GAGGCCAGAG GATGCTCCCC 2037       2047       2057       2067       2077       2087       2097
ATGCTGCCAC TATTTATTGT GAGCCCTGGA GGCTCCCATG TGCTTGAGGA AGGCTGGTGA GCCCGGCTCA 2107       2117       2127       2137       2147       2157       2167
GGACCCTCTT CCCTCAGGGG CTGCACCCTC CTCTCACTCC CTTCCATGCC GGAACCCAGG CCAGGACCC 2177       2187       2197       2207       2217       2227       2237
ACCGGCCTGT GGTTTGTGGG AAAGCAGGGT GGACGCTGAG GAGTGAAAGA ACCCTGCACC CAGAGGGCCT
```

Figure 1 (Con't)

```
       2247       2257       2267       2277       2287       2297       2307
   GCCTGGTGCC AAGGTATCCC AGCCTGGACA GGCATGGACC TGTCTCCAGA GAGAGGAGCC TGAAGTTCGT 2317       2327       2337       2347       2357       2367       2377
   GGGGCGGGAC AGCGTCGGCC TGATTTCCCG TAAAGGTGTG CAGCCTGAGA GACGGAAGA GGAGGCCTCT 2387       2397       2407       2417       2427       2437       2447
   GGACCTGCTG GTCTGCACTG ACAGCCTGAA GGGTCTACAC CCTCGGCTCA CCTAAGTGCC CTGTGCTGGT 2457       2467       2477       2487       2497       2507       2517
   TGCCAGGCGC AGAGGGGAGG CCAGCCCTGC CCTCAGGACC TGCCTGACCT GCCAGTCATG CCAAGAGGGG 2527       2537       2547       2557       2567       2577       2587
   GATCAAGCAC TGGCCTCTGC CCCTCCTCCT TCCAGCACCT GCCAGAGCTT CTCCAGGAGG CCAAGCAGAG 2597       2607       2617       2627       2637       2647       2657
   GCTCCCCTCA TGAAGGAAGC CATTGCACTG TGAACACTGT ACCTGCCTGC TGAACAGCCT GCCCCCGTCC 2667       2677       2687       2697       2707       2717       2727
   ATCCATGAGC CAGCATCCGT CCGTCCTCCA CTCTCCAGCC TCTCCCCAGC CTCCTGCACT GAGCTGGCCT 2737       2747       2757       2767       2777       2787       2797
   CACCAGTCGA CTGAGGGAGC CCCTCAGCCC TGACCTTCTC CTGACCTGGC CTTTGACTCC CGGAGTGGA 2807       2817       2827       2837       2847       2857       2867
   GTGGGTGGG AGAACCTCCT GGGCCGCCAG CCAGAGCCGG TCTTTAGGCT GTGTTGTTCG CCCAGGTTTC 2877       2887       2897       2907       2917       2927       2937
   TGCATCTTGC ACTTTGACAT TCCAAGAGG GAAGGGACTA GTGGGAGAGA GCAAGGGAGG GGAGGGCACA 2947       2957       2967       2977       2987       2997       3007
   GACAGAGAGG CTACAGGGCG AGCTCTGACT GAAGATGGGC CTTTGAAATA TAGGTATGCA CCTGAGGTTG 3017       3027       3037       3047       3057       3067       3077
   GGGAGGGTC TGCACTCCCA AACCCAGCG CAGTGTCCTT TCCCTGCTGC CGACAGGAAC CTGGGGCTGA 3087       3097       3107       3117       3127       3137       3147
   GCAGGTTATC CCTGTCAGGA GCCCTGGACT GGGCTGCATC TCAGCCCCAC CTGCATGGTA TCCAGCTCCC
```

Figure 1 (Con't)

```
        3157       3167       3177       3187       3197       3207       3217
   ATCCACTTCT CACCCTTCTT TCCTCCTGAC CTTGGTCAGC AGTGATGACC TCCAACTCTC ACCCACCCC 3227       3237       3247       3257       3267       3277       3287
   TCTACCATCA CCTCTAACCA GGCAAGCCAG GGTGGGAGAG CAATCAGGAG AGCCAGGCCT CAGCTTCCAA 3297       3307       3317       3327       3337       3347       3357
   TGCCTGGAGG GCCTCCACTT TGTGGCCAGC CTGTGGTGGT GGCTCTGAGG CCTAGGCAAC GAGCGACAGG 3367       3377       3387       3397       3407       3417       3427
   GCTGCCAGTT GCCCCTGGGT TCCTTTGTGC TGCTGTGTGC CTCCTCTCCT GCCGCCCTTT GTCCTCCGCT 3437       3447       3457       3467       3477       3487       3497
   AAGAGACCCT GCCCTACCTG GCCGCTGGGC CCCGTGACTT TCCCTTCCTG CCCAGGAAAG TGAGGGTCGG 3507       3517       3527       3537       3547       3557       3567
   CTGGCCCCAC CTTCCCTGTC CTGATGCCGA CAGCTTAGGG AAGGGCAGTG AACTTGCATA TGGGCTTAG 3577       3587       3597       3607       3617       3627       3637
   CCTTCTAGTC ACAGCCTCTA TATTTGATGC TAGAAAACAC ATATTTTTAA ATGGAAGAAA AATAAAAAGG 3647       3657       3667       3677       3687       3697       3707
   CATTCCCCCT TCATCCCCCT ACCTTAAACA TATAATATTT TAAAGGTCAA AAAAGCAATC CAACCCACTG 3717       3727       3737       3747       3757       3767       3777
   CAGAAGCTCT TTTTGAGCAC TTGGTGGCAT CAGAGCAGGA GGAGCCCCAG AGCCACCTCT GGTGCCCCC 3787       3797       3807       3817       3827       3837       3847
   CAGGCTACCT GCTCAGGAAC CCCTTCTGTT CTCTGAGAAG TCAAGAGAGG ACATTGGCTC ACGCACTGTG 3857       3867       3877       3887       3897       3907       3917
   AGATTTTGTT TTTATACTTG GAAGTGGTGA ATTATTTTAT ATAAAGTCAT TTAAATATCT ATTTAAAAGA 3927       3937       3947       3957       3967       3977
   TAGGAAGCTG CTTATATATT TAATAATAAA AGAAGTGCAC AAGCTGCCGT TGACGTAGCT CGAG
```

HEMATOPOIETIC GROWTH FACTORS

This application is a continuation-in-part of Ser. No. 860,377 filed May 6, 1986.

The present invention relates to a novel family of CSF-1-like hematopoietic growth factors, and a process for producing them by recombinant genetic engineering techniques.

BACKGROUND

Hematopoietins, i.e., hematopoietic growth factors, are proteins that promote the survival, growth and differentiation of hematopoietic cells. Colony stimulating factors (CSFs) are a subset of these hematopoietic growth factors tht are characterized by the ability to support the growth, *in vitro*, of colonies of hematopietic cells arising from progenitor cells of bone marrow, fetal liver and other hematopoietic organs.

The biochemical and biological identification and characterization of certain hematopoietins has been hampered by the small quantities of the naturally occurring factors available from natural sources, e.g., blood and urine. With recombinant genetic engineering techniques, however, some of these hematopoietins have been molecularly cloned, heterologously expressed and purified to homogeneity. [See D. Metcalf, "The Molecular Biology and Functions of the Granulocyte-Macrophage Colony Stimulating Factors," *Blood*, 67(2):257–267 (1986).] Among these hematopoietins are human and murine GM-CSF, human G-CSF, human CSF-1 and murine IL3. Human IL-3 has also recently been identified [Y. C. Yang et al., *Cell*, 47(1):3–10 (1986)]. Both human GM-CSF [See, R. Donahue et al., *Nature*, 321:872–875 (1986)] and murine IL3 [See J. Kindler et al, *Proc. Natl. Acad. Sci. U.S.A.*, 83:1001–1005 (1986)] have a demonstrated effect on hematopoiesis *in vivo*.

A cDNA sequence for human urinary CSF-1 has been reported by E. S. Kawasaki, et al., *Science*, 230:291–296 (1985) [hereinafter "Kawasaki"], which, when expressed in a COS cell transient expression system, produced a 26 kD protein that competed with labeled murine CSF-1 in a radioreceptor assay. The protein also reportedly stimulated mouse bone marrow proliferation, resulting in predominantly monocytic lineage type colonies in the mouse bone marrow assay. The protein biological activity was reportedly inhibited by neutralizing antisera for CSF-1.

BRIEF SUMMARY OF THE INVENTION

As one aspect of the invention, a family of CSF-1-like growth factors are provided which are characterized by the amino acid sequences shown in FIG. 1, below. The amino acid sequences of the growth factors of the present invention are encoded by the DNA sequences also illustrated in FIG. 1. Similarly, DNA sequences which code for polypeptides coded for by the sequences of FIG. 1, but which differ in codon sequence due to the degeneracies of the genetic code or differ in nucleotide sequence due to cross-species variation or induced modifications also encode the novel growth factors of this family described herein.

In addition to the DNA sequence homology to the sequences of FIG. 1, the members of this novel family of growth factors are also characterized by having at least one biological property of a CSF-1-like growth factor. Preferably more than one CSF-1-like biological property is demonstrated by any one member of the family of growth factors of the present invention.

"CSF-1-like biological property" is defined herein to include one or more of the following biological characteristics and *in vivo* and *in vitro* activities. One such property is the support of the growth and differentiation of progenitor cells committed to the monocyte lineages. For example, in a standard human bone marrow assay, a CSF-1-like biological property is the stimulation of macrophage colonies. Another CSF-1-like biological property is complete inactivation by preincubation with 2-mercaptoethanol or an excess of rabbit antiserum raised to purified human urinary CSF-1. Additionally, CSF1-like properties include the ability to stimulate monocytes to produce other CSF-like factors e.g. myeloid CSF, TNF and interfeon activity which interact with accessory and mature cells. Further CSF-1-like biological properties are the stimulation of biological activities of mature macrophages and the cells of continuous macrophage-like cell lines. Yet another CSF-1-like biological property is an apparent molecular weight of about 50 to 90 kd by non-reducing sodium dodecyl sulfate polyacrylamide gel electrophoresis (SDS-PAGE). Other biological properties attributed to CSF-1 have been disclosed in the art.

As a further aspect of the present invention there are provided novel cDNA sequences coding on expression for CSF1-like polypeptides or growth factors. These DNA sequences include those depicted in FIG. 1 in a 5' to 3' direction and those sequences described above. Variations in the DNA sequences of FIG. 1 which are caused by point mutations or by induced modifications to enhance the activity or production of the polypeptides are also encompassed in the invention. Similarly, synthetic polypeptides which wholly or partially duplicate continuous sequences of the amino acid residues of FIG. 1 are also part of this invention. These sequences, by virtue of sharing primary, secondary or tertiary structural and conformational characteristics with naturally-occurring CSF-1-like polypeptides of the invention may possess biological activity and/or immunological properties in common with the naturally-occurring product. Thus, they may be employed as biologically active or immunological substitutes for naturally-occurring primate CSF-1-like polypeptides in therapeutic and immunological processes.

As another aspect of the present invention, there is provided a novel method for producing the novel family of CSF-1-like growth factors. The method of the present invention involves culturing a suitable cell or cell line, which has been transformed with a vector containing a cDNA sequence coding on expression for a novel CSF-1-like polypeptide. Suitable cells or cell lines may be mammalian cells, such as Chinese hamster ovary cells (CHO). Another suitable mammalian cell line, which is described in the accompanying examples, is the monkey COS-1 cell line. A similarly useful mammalian cell line is the CV-1 cell line. Also suitable for use in the present invention are bacterial cells. For example, the various strains of *E. coli* are well-known as host cells in the field of biotechnology. Various strains of *B. subtilis* may also be employed in this method. Many strains of yeast cells known to those skilled in the art are also available as host cells for expression of the polypeptides of the present invention. Additionally, where desired, insect cells may be utilized as host cells in the method of the present invention.

Another aspect of the present invention provides vectors for use in the method of expression of these novel polypeptides. These vectors contain the novel DNA sequences described above which code for the novel polypeptides of the invention. Alternatively, vectors incorporating modified sequences as described above are also embodiments of the present invention and useful in the production of these CSF-1-like polypeptides. The vector employed in the method also contains selected regulatory sequences in operative association with the DNA coding sequences of the invention and capable of directing the replication and expression thereof in selected host cells. A variety of such regulatory sequences useful in the vectors of the present invention are well known to those skilled in the art.

The members of the novel family of CSF-1-like growth factors may be used in the treatment of diseases characterized by a decreased level of hematopoietic cells, particularly those of myeloid, and moncyte lineages. These factors may be used to directly stimulate monocyte and macrophage production and may indirectly stimulate other hematopoietic lineages. Among conditions susceptible to treatment with the polypeptides of the present invention is leukopenia, a reduction in the number of circulating leucocytes (white cells) in the peripheral blood. Leukopenia may be induced by exposure to certain viruses or to radiation. It is often a side effect of various forms of cancer therapy, e.g., exposure to chemotherapeutic drugs. Therapeutic treatment of leukopenia with these CSF-1-like polypeptide compositions may avoid undesirable side effects caused by treatment with presently available drugs.

In addition these polypeptides may serve as activators of mature white cells in cases of serious infection. These factors may be employed to treat infectious diseases characterized by intracellular parasitism, e.g., viral infections (herpes, cytomgalovirus), bacterial infections (Mycobacterium, Listeria), fungal infections (Candida) and parasitic infections (Malaria) and the like.

Alone, or in combination with other hematopoietins, these factors enhance macrophage function causing the activated macrophages to kill tumor cells, to release alpha-interferon, to kill parasites or to release and enhance other CSFs which may stimulate the proliferation and activation of other blood cells.

The polypeptides of the present invention may also be employed, alone or in combination with other hematopoietins, in the treatment of other blood cell deficiencies, including thrombocytopenia (platelet deficiency), or anemia (red cell deficiency). Other uses for these novel polypeptides are in the treatment of patients recovering from bone marrow transplants, enhancing host defense during surgery and in burn patients. These factors may also be employed to develop monoclonal and polyclonal antibodies generated by standard methods for diagnostic or therapeutic use.

Therefore, as yet another aspect of the invention are therapeutic compositions for treating the conditions referred to above. Such compositions comprise a therapeutically effective amount of one or more of the members of the family of CSF-1-like polypeptides of the present invention in admixture with a pharmaceutically acceptable carrier. This composition can be systematically administered either parenterally, intraveneously or subcutaneously. When systematically administered, the therapeutic composition for use in this invention is, of course, in the form of a pyrogen-free, parenterally acceptable aqueous solution. The preparation of such a parenterally acceptable protein solution, having due regard to pH, isotonicity, stability and the like, is within the skill of the art.

The dosage regimen will be determined by the attending physician considering various factors which modify the action of drugs, e.g. the condition, body weight, sex, and diet of the patient, the severity of any infection, time of administration and other clinical factors. Generally, the daily regimen should be in the range of 1–1000 micrograms of polypeptide or 50 to 5000 units (ie, a unit being the concentration of polypeptide which leads to half maximal stimulation in a standard murine bone marrow assay) of polypeptide per kilogram of body weight. This therapeutic composition may also be administered in conjunction with other human factors. A non-exclusive list of other appropriate hematopoietins, CSFs and interleukins for interaction with the polypeptides of the present invention includes GM-CSF, G-CSF, Meg-CSF, erythropoietin (EPO), IL-1, IL-3, other CSF-1-like polypeptides, H-1, IL-4, IL-2, B-cell growth factor, B-cell differentiation factor and eosinophil differentiation factor. The dosage recited above would be adjusted to compensate for such additional components in the therapeutic composition. Progress of the treated patient can be monitored by periodic assessment of the hematological profile, e.g. white cell count and the like.

DETAILED DESCRIPTION OF THE INVENTION

The present invention provides a family of CSF-1-like growth factors characterized by amino acid sequences substantially homologous to the amino acid sequences illustrated in FIG. 1. These sequences may be encoded by the DNA sequences depicted in the Table or variously modified sequences as described above. These polypeptides are also characterized by CSF-1-like biological properties.

The specific sequences illustrated in FIG. 1 are exemplary members of the growth factor family of the present invention. The 4 kb DNA of FIG. 1 codes on expression for a novel CSF-1-like protein, named CSF-69. It was isolated from poly A+mRNA of the SV40 transformed trophoblast cell line TPA30-1 [ATCC #CRL-1583]. The sequence of FIG. 1 contains a long open translational reading frame of 1662 nucleotides, encoding a 554 amino acid polypeptide. The protein coding region of the 4 kb sequence extends from nucleotide #146 (methionine at −32) to nucleotide #1807 which is followed by a TAG stop codon. There are four potential asparagine-linked glycosylation sites illustrated by the characteristic sequences, Asn-X-Ser or Asn-X-Thr. The remaining 2200 nucleotides of 3' non-coding sequence of the 4 kb region may have a regulatory role in transcription in the natural host. The 3' end of the sequence also contains an AT-rich segment including several repeats of the sequence ATTTA, which is believed to be related to the RNA message stability [See, G. Shaw and R. Kamen, *Cell*, 46(5):659–677 (1986)].

This sequence contains three portions, i.e. from nucleotide #1 to #415, from nucleotide #419 to #689 and from nucleotide #1584 to #1823, which are found in the sequence of Kawasaki et al., *supra*. The coding region of the CSF-1 described by Kawasaki et al., differs from that described herein by the deletion of 894 bp between nucleotides #689 and #1584 recited in FIG. 1.

This approximately 4 kb DNA sequence is harbored in plasmid p3ACSF-69 in *E. coli* HB 101, which was deposited in the American Type Culture Collection, 12301 Parklawn Dr., Rockville, MD on Apr. 16, 1986 and given accession number ATCC 67092.

The 4 kb sequence of FIG. 1 codes on expression for one novel CSF-1-like protein of the present invention, CSF-69. CSF-69 is characterized by an apparent molecular weight of approximately 70–90 kD when analyzed by polyacrylamide gel electrophoresis under non-reducing conditions. However, if this analysis is performed after reduction of the CSF-69, the protein is characterized by an apparent molecular weight of 35–45 kD suggesting that CSF-69 is a disulfide linked homo-dimer of 35–45 kD subunits. In p3ACSF-69 conditioned media, CSF-69 demonstrated CSF-1-like activity in *in vitro* mouse and human bone marrow assays.

The approximately 61 kD precursor encoded by the sequence of FIG. 1 is processed at the amino terminus by removal of a 32 residue signal peptide and in the carboxy terminal region by removal of about 333 residues to yield a subunit of approximately 189 amino acids with a predicted molecular weight of 21 kD. Thus the mature CSF-1 monomer has Glu at its amino terminal and extends at least through to amino acid Leu at position #189 (See FIG. 1). This subunit retains two of the four potential sites for addition of asparagine-linked carboyhydrate that are present in the sequence of FIG. 1. Glycosylation of the 21 kD polypeptide at these two positions is presumed to account for most of the remaining mass of the 35–45 kD subunit of CSF-69.

Other novel CSF-1-like proteins of the present invention are encoded by only a portion of the sequence of FIG. 1. One such CSF-1-like protein is encoded by nucleotides 1 to 1332 of the cDNA sequence of FIG. 1 and has activity, upon expression, in the murine bone marrow assay described below. Similarly, cDNA sequences of from nucleotides 1 to 699, from nucleotides 1 to 881 and from nucleotides 1 to 1012, when blunted and inserted into the expression vector described below also produced active protein. Additionally, another full length cDNA clone had a cytosine at position 1678 of FIG. 1, rather than a thymidine. This change conserved the amino acid, alanine, in the sequence.

The family of CSF-1-like growth factors provided herein also includes factors encoded by the sequences of FIG. 1 into which nucleotide modifications have been deliberately engineered. Such modifications in the DNA sequences can be made by one skilled in the art using various techniques. Specific modifications of interest in these CSF-1-like related sequences include the replacement of one or more of the cysteine residues in the coding sequences with other amino acids, e.g. serine, to eliminate a disulfide bridge. The 699 nucleotide factor, for example, has eliminated several of the cysteines entirely. Mutagenic techniques for such replacement are well known to one skilled in the art. [See, e.g., U.S. Pat. No. 4,518,584.]

Other specific mutations of the sequences of the CSF-1-like factors described herein involve modifications of one or both of the glycosylation sites. The absence of glycosylation or only partial glycosylation results from amino acid substitution at one or both of the asparagine-linked glycosylation recognition sites present in the sequences of the CSF-1-like factors shown in FIG. 1. These tripeptide sequences are either asparagine-X-threonine or asparagine-X-serine, where X is usually any amino acid. A variety of amino acid substitutions at one or more of the three amino acid positions of a glycosylation recognition site, especially the first and-/or third such positions, result in non-glycosylation at the modified tripeptide sequence. By way of example, $Asn_{122}$ of the sequence of FIG. 1 can be replaced with glutamine in one such modified CSF-1-like factor. The resulting factor ($Gln_{122}$) should contain only one asparagine-linked carbohydrate moiety rather than two such moieties. Those skilled in the art will appreciate that analogous glycoproteins having the same mono-glycosylation may be prepared by substituting another amino acid at position 122, and/or by substituting other amino acids at the other positions within the glycosylation recognition sites, e.g., inserting valine at $Thr_{124}$. Similarly, the Asn at position 122 and/or Thr at position 124 may be altered by a mutagenic technique to other amino acids to deglycosylate the factor at that site. Alternatively, both of the sites may be altered as above. [See, e.g. A. Miyajima et al., *EMBO J.*, 5(6):1993–1197 (1986)].

The following examples illustrate the method of the present invention employing the DNA sequence of FIG. 1 to produce CSF-69.

EXAMPLE I

Construction of an exemplary mammalian expression vector p3ACSF-69

To construct a mammalian vector for expression of a novel CSF-1-like protein, the cDNA sequence depicted in FIG. 1 above was adapted with restriction endonuclease enzyme XhoI linkers (New England Biolabs) and ligated into XhoI-digested, phosphatased COS cell expression vector pXM. pXM contains the SV40 enhancer, major adenovirus late promoter, DHFR coding sequence, SV40 late message poly A addition site and VaI gene. pXM further contains a linker sequence with restriction endonuclease sites for KpnI, PstI and XhoI. The plasmid resulting from the XhoI digestion of pXM and the insertion of the linker and the XhoI adapted DNA sequence of FIG. 1 coding for a CSF-like protein was designated p3ACSF-69. p3ACSF-69 (ATCC #67092) can be transformed by conventional techniques into a suitable mammalian host cell for expression of the CSF-like protein. Exemplary host cells are mammalian cells and cell lines, particularly primate cell lines, rodent cell lines and the like.

A similar expression vector may also be prepared containing the other, CSF-1-like sequences identified above, or containing only the amino acid coding regions of those sequences of FIG. 1, with the 5' and 3' non-coding regions deleted. One skilled in the art can construct other mammalian expression vectors comparable to p3ACSF-69 by cutting the DNA sequence of FIG. 1 from the plasmid with XhoI and employing well-known recombinant genetic engineering techniques and other known vectors, such as pCD [Okayama et al., *Mol. Cell Biol.* 2:161–170 (1982)] and pJL3, pJL4 [Gough et al., *EMBO J.* 4:645–653 (1985)]. The transformation of these vectors into appropriate host cells can result in expression of a CSF-1-like protein.

Similarly, one skilled in the art could manipulate the CSF-1-like sequences by eliminating or replacing the mammalian regulatory sequences flanking the coding sequence with yeast, bacterial or insect sequences to create non-mammalian vectors. Thus this sequence would then be expressable in yeast, bacterial or insect host cells. For example, the coding sequence of FIG. 1 could be cut from p3ACSF-69 with XhoI and further manipulated (e.g., ligated to other known linkers or modified by deleting non-coding sequences therefrom or altering nucleotides therein by other known techniques). The modified CSF coding sequence could then be inserted into, for example, a known bacterial vector using procedures such as described in T. Taniguchi et al, *Proc. Natl. Acad. Sci U.S.A.*, 77:5230–5233 (1980). This exemplary bacterial vector could then be transformed into bacterial host cells and the CSF-69 protein expressed thereby.

Similar manipulations can be performed for the construction of an insect vector [See, e.g., procedures described in published European patent application 155,476] or a yeast vector [See, e.g., procedures described in published PCT application WO 86 00639] for expression of the CSF-1-like proteins in insect or yeast cells.

EXAMPLE II

Expression of a CSF-1-like Protein

Plasmid DNA, prepared from *E. coli* HB101 containing p3ACSF-69 as described in Maniatis et al., *Molecular Cloning, A Laboratory Manual*, Cold Spring Harbor Laboratory, (1982) was purified by conventional methods involving equilibrium centrifugation in cesium chloride gradients containing ethidium bromide COS cells (ATCC CRL 1650) were transfected with the purified DNA at a concentration of approximately 5 ug plasmid DNA per 106 COS cells and treated with chloroquine according to the procedures described in G. G. Wong et al., *Science*, 280:810–815 (1985) and R. J. Kaufman et al., *Mol. Cell Biol.*, 2:1304 (1982). 72 hours following transfection, p3ACSF-69 medium can be harvested containing a protein which demonstrates CSF-1-like activity in standard bone marrow assays, as discussed in Example III below.

EXAMPLE III

CSF Activity in *In Vitro* Assays

A. Mouse assay

Mouse bone marrow assays were conducted as described in D. Metcalf, *The Hemopoietic Colony Stimulating Factors*, Elsevier Press, New York (1984) with the following modifications:

(a) $2\times10^5$ bone marrow cells per ml were employed in the assay;

(b) final assay volume was 100 ul; and (c) assays were set up in standard 96 well microtitre plates.

Bone marrow was obtained from the femurs of 6–25 week old female Balb/c mice (Jackson). Using WEHI 3 conditioned medium [J. C. Lee et al., *J. Immunol.*, 128:2393–2398 (1982)]which contains mouse L cell conditioned medium as a standard control, one dilution unit of activity was defined as that concentration of protein which results in a maximal response in this bone marrow assay, i.e., approximately 15 to 20 colonies per $2\times10^4$ mouse bone marrow cells.

p3ACSF-69 conditioned medium was found to be active to at least $1:10^4$ dilution in a mouse bone assay and produced mainly monocytic lineage type colonies. The number and type of cells in a maximal response will vary with the strain and age of the mouse donors.

B. Human Assay

Human bone marrow assays, employing non-adherent bone marrow cells, were performed as described in G. G. Wong, et al, *supra*. p3ACSF-69 conditioned medium was active to a 1:50 dilution in human bone marrow assays and produced predominantly monocytic lineage-type colonies.

EXAMPLE IV

Construction of CHO cell lines expressing hiqh levels of CSF-69

One method for producing high levels of the CSF-1-like polypeptides from mammalian cells involves the construction of cells containing multiple copies of the heterologous CSF-1-like gene. The heterologous gene can be linked to an amplifiable marker, e.g., the dihydrofolate reductase (DHFR) gene for which cells containing increased gene copies can be selected by propagation in increasing concentrations of methotrexate (MTX) according to the procedures of Kaufman & Sharp, *J. Mol. Biol., supra.* This approach can be employed with a number of different cell types.

p3aMCSF R1 #1–69 and the DHFR expression plasmid pAdD26SV (A)3 (Kaufman & Sharp, *Mol. Cell Biol., supra*) were co-transfected into DHFR-deficient CHO cells, DUKX-BII, by calcium phosphate coprecipitation and transfection. The initial DHFR expressing transformants were selected for growth in alpha media with dialyzed fetal calf serum, and subsequently selected for amplification by growth in increasing concentrations of MTX as described in Kaufman, et al., *Mol. Cell Biol.* 5:1750 (1983).

One clone, designated 5/9 mα3–18 (0.2) (ATCC No CRL 10154) which was selected for growth in 0.2 micromolar MTX was found to express high levels of biologically active CSF-69. This cell line consistently generated conditioned medium which was active in supporting murine macrophage colony formation at a 1:60,000 final dilution. These cells (one 10 cm dish) as well as the parent CHO cells were labeled with 1 mCi of $^{35}$S-met (NEN) in 4 ml of Minimal Essential Medium (MEM) for 4 hours at 37° C. The resulting conditioned media samples were incubated with antiserum raised in rabbits with purified urinary CSF-1. The antigen-antibody complexes were precipitated by adsorbtion to *Staphylococcus aureus* cells (Cal Biochem). The complexes were solubilized in a loading buffer lacking reducing agent according to U. K. Laemmli, *Nature*, 227: 680–685 (1970). To reduce samples they were brought to 100 mM 2-mercaptoethanol and incubated at 37° C. for 30 minutes. Following electrophoresis in 10% polyacrylamide gel, the pattern of labeled proteins were visualized by fluorography (Enhance, NEN) using Kodak XAR film.

Analysis of these immunoprecipitates by SDS polyacrylamide gel electrophoresis under non-reducing conditions revealed that the conditioned medium from the CSF-1-like protein producing CHO cells contained two heterogeneous CSF-1-like protein species of apparent sizes 70–90 kD and greater than 150 kD. The observed size heterogeneity of these CSF-1-like proteins is typical of many glycoproteins. Analysis of the same samples following reduction revealed that the mobility of the 70–90 kD species of CSF-1-like protein shifted to a position consistent with a molecular weight of 35–45 kD while the relative mobility of the larger species (greater than 150 kD) was unaffected by the treatment. Thus at least two different CSF-1-like proteins are expressed by the 5/9 mα3–18 (0.2) cells: a 70–90 kD protein comprising a disulfide linked dimer of a 35–45 kD subunit, and a much larger species.

EXAMPLE V

Purification of CSF-69

The CHO-cell conditioned media containing 0.5% fetal bovine serum and DMEM-F12 is diluted 1:1 with water. The diluted media is then applied to a QAE 'Zeta-Prep' cartridge (LKB) which is equilibrated in 40 mM Tris pH 7.4. The flow through containing unbound protein was discarded. Bound protein was washed with 40 mM Tris, pH 7.4 and eluted with 40 mM Tris, pH 7.4 and 0.75M NaCl. The eluate is then diluted with water to a concentration of 0.5M NaCl. Tween 20 was added to 0.05% and this mixture loaded at approximately 1 column volume/hour on to a lentil lectin. Sepharose 4B column [Pharmacia] which had been equilibrated in 20 mM Tris, pH 7.4, 0.5M NaCl and 0.05% Tween 20. The column was washed with 2–5 cv, 20 mM Tris, Ph 7.4, and 0.5 M NaCl. Specifically-bound protein was eluted with 20 mM Tris, 0.2M alpha methylmannopyranoside, 0.5M NaCl and 0.05% Tween 20, and then acidified with 10% trifluoroacetic acid [TFA]. The eluate was subjected to reverse phase liquid chromatography on a column equilibrated in 30% acetonitrile and 0.1% TFA. Protein was eluted with ascending acetonitrile in 0.1% TFA. Protein collected between 45 and 50% acetonitrile was neutralized in tubes with Tris, pH 8.5 and analyzed.

The preliminary analysis of CSF-69 reveals a specific activity of approximately $10^6$ bone marrow units per milligram [see bone marrow assay in Example III].

Numerous modifications and variations in practice of this invention are expected to occur to those skilled in the art upon consideration of the foregoing descriptions of preferred embodiments thereof. Such modifications and variations are believed to be encompassed in the appended claims.

What is claimed is:

1. A DNA sequence consisting essentially of a DNA coding on expression for a polypeptide capable of stimulating proliferation of monocytic cells in both humans and mouse bone marrow assays and having a peptide sequence encompassing the mature form of the polypeptide of FIG. 1 and allelic variations thereof also capable of stimulating proliferation of monocylic cells in both human and mouse bone marrow assays.

2. A transformation vector comprising a DNA sequence according to claim 1 in operative association with an expression control sequence therefor.

3. The vector according to claim 2, which is p3ACSF-69.

4. A host cell containing the vector of claim 2 and being capable of producing said polypeptide.

* * * * *